United States Patent
Pettersson

(10) Patent No.: US 6,280,616 B1
(45) Date of Patent: *Aug. 28, 2001

(54) COLUMN FOR CHROMATOGRAPHY

(75) Inventor: Conny Pettersson, Hässelby (SE)

(73) Assignee: Pharmacia Biotech AB, Uppsala (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,130

(22) PCT Filed: Feb. 16, 1996

(86) PCT No.: PCT/SE96/00206

§ 371 Date: Aug. 13, 1997

§ 102(e) Date: Aug. 13, 1997

(87) PCT Pub. No.: WO96/26436

PCT Pub. Date: Aug. 29, 1996

(30) Foreign Application Priority Data

Feb. 21, 1995 (SE) .................................................. 9500635

(51) Int. Cl.[7] ................................................. B01D 15/08
(52) U.S. Cl. ..................... 210/198.2; 210/635; 210/656
(58) Field of Search ............................... 210/198.2, 635, 210/656, 502.1; 95/88, 85; 96/101, 105, 107

(56) References Cited

U.S. PATENT DOCUMENTS

| | | | | |
|---|---|---|---|---|
| 3,682,315 | * | 8/1972 | Haller | 210/198.2 |
| 3,796,657 | * | 3/1974 | Pretorius | 210/198.2 |
| 3,926,800 | * | 12/1975 | Stephens | 210/198.2 |
| 4,470,910 | | 9/1984 | Quemerais et al. | 210/198.2 |
| 4,557,830 | | 12/1985 | Onitsuka et al. | 210/198.2 |
| 4,582,608 | * | 4/1986 | Ritacco | 210/198.2 |
| 4,587,014 | | 5/1986 | America | 210/198.2 |
| 4,732,687 | * | 3/1988 | Muller | 210/198.2 |
| 4,737,292 | * | 4/1988 | Ritacco | 210/198.2 |
| 4,743,373 | * | 5/1988 | Rai | 210/198.2 |
| 4,882,047 | * | 11/1989 | Shalon | 210/198.2 |
| 4,894,152 | * | 1/1990 | Colvin | 210/198.2 |
| 5,141,635 | * | 8/1992 | LePlang | 210/198.2 |
| 5,167,810 | * | 12/1992 | Vassarotti | 210/198.2 |
| 5,282,973 | * | 2/1994 | Mann | 210/198.2 |
| 5,316,821 | * | 5/1994 | Otani | 210/198.2 |
| 5,324,426 | * | 6/1994 | Joseph | 210/198.2 |
| 5,338,448 | * | 8/1994 | Gjerde | 210/198.2 |
| 5,772,875 | * | 6/1998 | Petterson | 210/198.2 |

FOREIGN PATENT DOCUMENTS 2248027A   3/1992 (GB) .

* cited by examiner

Primary Examiner—Ernest G. Therkorn
(74) Attorney, Agent, or Firm—Birch, Stewart, Kolasch & Birch, LLP

(57) ABSTRACT

Disclosed is a chromatography column having adapters that include an end-plate and a perforated plate such as to form a gap between the end-plate and the perforated plate. The column is particularly suited for large-scale chromatography in which matrices of small particle sizes are used.

13 Claims, 3 Drawing Sheets

COLUMN FOR CHROMATOGRAPHY

REFERENCE TO RELATED APPLICATIONS

This application is a 371 of PCT/SE96/00206 filed Feb. 16, 1996.

TECHNICAL FIELD

The present invention relates to a column for liquid chromatography.

1. Description of Known Techniques

When practicing liquid chromatography on a porous matrix, a liquid containing a dissolved compound is allowed to pass through the matrix, wherewith the compound flows through the matrix while passing through one or more adsorption/desorption stages.

Matrices intended for liquid chromatography are normally comprised of particles, e.g. beads, that are packed together in a column tube to form a bed. The bed is normally held in place in the tubular column with the aid of two adapters, each covering a respective end of the bed and therewith also the cross-sectional area of the column. One of the adapters will often include an inlet for elution agent which prior to penetrating the matrix bed passes through a perforated plate which distributes the flow uniformly over the end area of the bed. The other adapter has an outlet for elution agent, which prior to entering the outlet also passes through a perforated plate which gathers the flow uniformly across the end area of the bed prior to the elution agent exiting through the outlet. It is normal to place a very fine net between the perforated plate and the gel bed, to prevent the ingress of gel material into respective adapters. Examples of perforated plates are filter plates, gratings, coarse nets, apertured plates and discs.

With the intention of minimizing diffusion and zone spreading during chromatography, the perforated plate, either with or without a fine net, is placed tightly against the inlet area of the bed at respective ends of the column. This is done to obviate the risk of particles swirling up from the bed.

According to known technique, perforated plates are placed against the gel bed and immediately adjacent the end-plate of respective adapters.

2. The Problems of Known Techniques

Conventional perforated plates, such as gratings, etc., have been found to present problems in large scale chromatographic processes in which the gel matrix consists of small beads, which require greater bed packing pressures and are operated at high rates of flow. By large-scale columns is meant here column tubes that have a diameter greater than or equal to 50 mm. A test which functions well on a small scale will often present problems in large-scale chromatography performed under the aforesaid conditions.

More specifically, the earlier known perforated plates impede the radial flow of eluting solution and sample solution respectively in the end-areas of the column, giving rise to an uneven plug flow. This uneven plug flow will often result in a more rapid flow in the middle of the column and slower flow out towards the periphery of the gel-bed cross-section. This is shown in the chromatogram by broad peaks with high degrees of dilution. The plate number of the column will therewith be lowered. Because of the high packing pressure necessary under these conditions, the conventional perforated plates are pressed tightly against the adapter end-plate.

DISCLOSURE OF THE INVENTION

It has now been found that a more uniform plug flow and an increase in plate number can be achieved in large-scale chromatography when a liquid gap is provided between the adapter end-plate and the perforated plate during the chromatographic process. This gap is obtained by providing a perforated plate with projections which function to generate a gap, in addition to openings. The positive effect obtained is because liquid that enters the adapter is spread radially through the perforated plate and penetrates the matrix, through the plate openings, in a continuous vertical layer across the end-area of the matrix, resulting in a uniform plug flow and a higher bottom number.

The inventive liquid-chromatographic column is comprised of a tube which contains a chromatographic gel matrix and an adapter placed at the inlet and the outlet of the column respectively. The invention is characterized in that at least one of the adapters, preferably the inlet adapter, includes a perforated plate and an end-plate, and in that a gap is formed between the end-plate and the perforated plate.

BRIEF DESCRIPTION OF THE DRAWINGS

The invention will now be described in more detail with reference to the accompanying drawings, in which.

DESCRIPTION OF THE PREFERRED EMBODIMENTS

Figure 1:
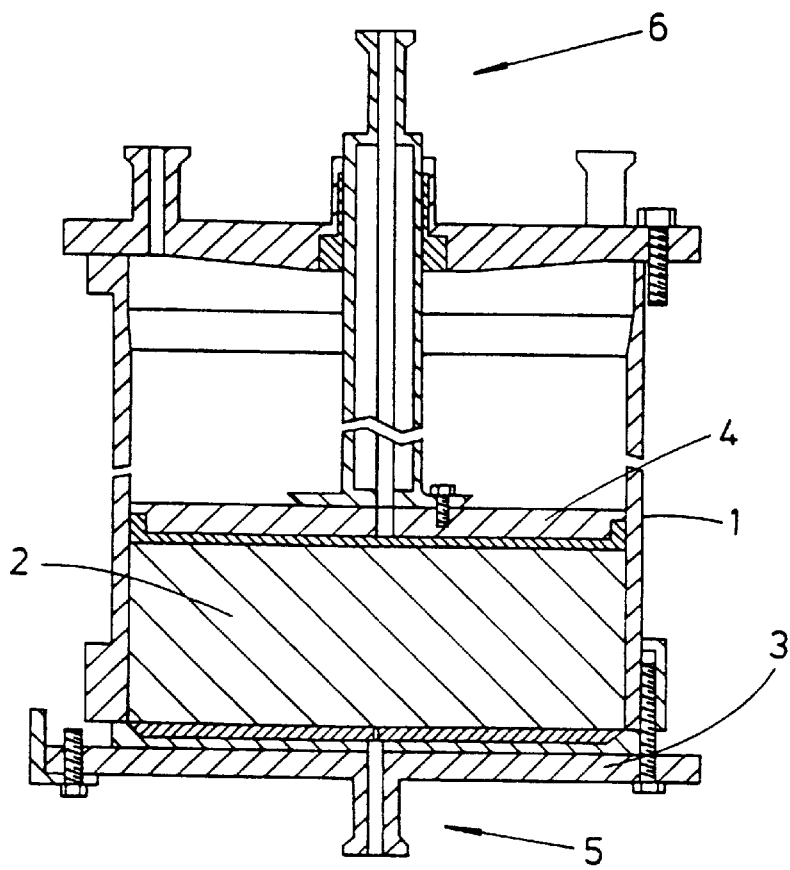
FIG. 1 illustrates one embodiment of an inventive column with applied flow.

FIG. 1 illustrates a column tube 1 filled with a matrix 2 and including two adapters 3 and 4 which respectively cover the inlet and outlet areas of the matrix. The adapters 3, 4 include respectively a liquid flow inlet 5 and a liquid flow outlet 6. The flow direction is arrowed in FIG. 1. Each of the adapters 3 and 4 is provided with a conventional sealing element, e.g. O-rings, which seal against the inner surface of the column 1.

Figure 2:
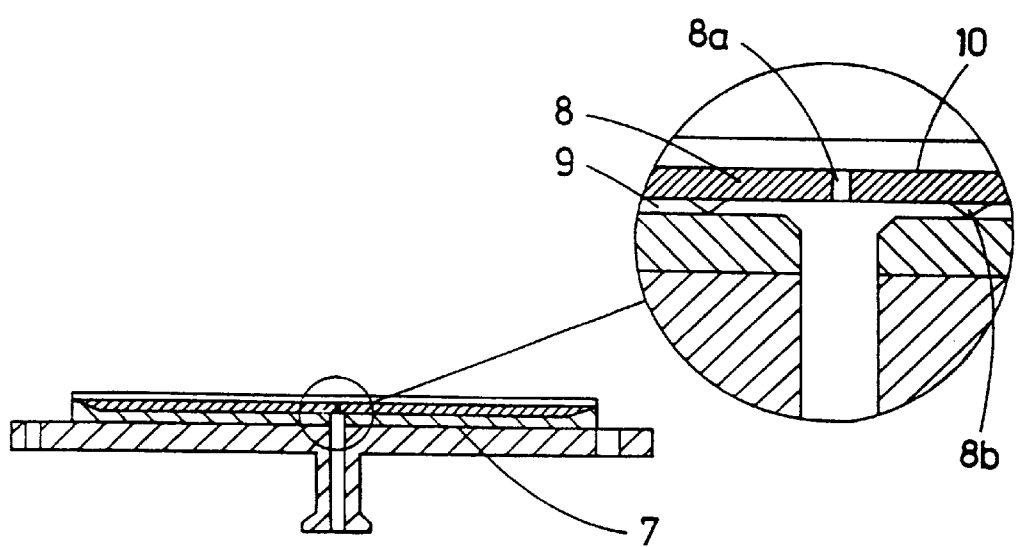
FIG. 2 is a cross-sectional view of the adapter.
Figure 3:
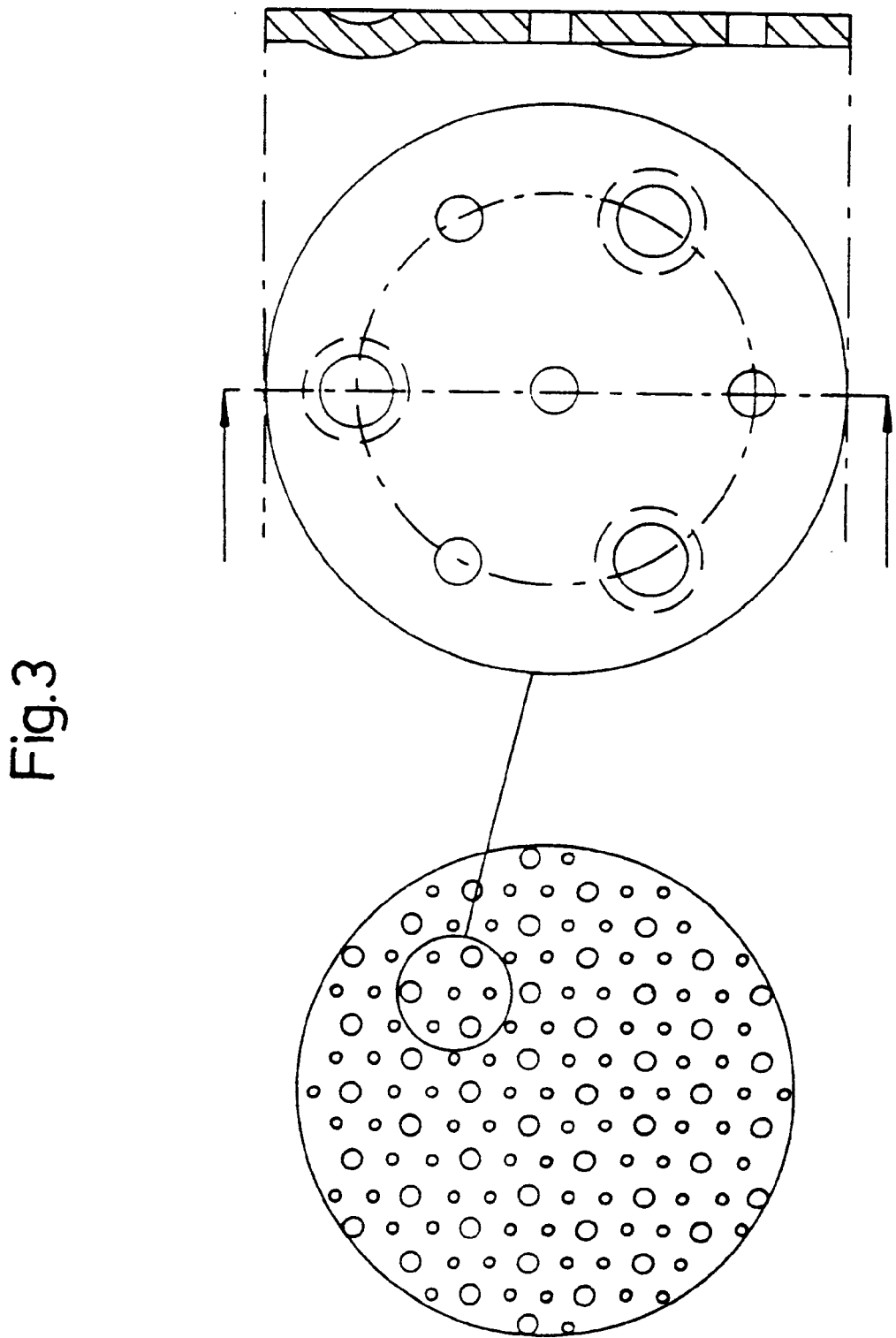
FIG. 3 is a view of the perforated plate from above.

The adapters 3 and 4 are shown in larger scale in FIG. 2, and include an end-plate 7 and a perforated plate 8 provided with openings 8a and projections 8b. The projections may alternatively be disposed on the end-plate of the adapter. The end-plate 7 and the perforated plate 8 define therebetween a gap 9, preferably a gap of from 0.2 to 1.0 mm in depth. The density of the projections is determined by the pressure at which the bed is packed, i.e. the greater the packing pressure, the denser the projections. It is essential that the gap depth will permit the flow to be uniformly distributed through the area of the perforated plate 8 when the column is packed. If the gap depth is excessively small, the flow will be distributed unevenly across the surface area of the plate. The gap depth will normally be >0.2 mm. The projections serve two purposes. Firstly, the projections will function as gap forming elements, and secondly shall exert the least possible resistance to radial flow, i.e. shall permit the incoming and outgoing flow to change direction through 90°. Appropriate shapes of the projections are therefore circular, oval, etc. According to one preferred embodiment of the invention, the projections are round.

A fine-mesh net 10 is preferably placed against the perforated plate, i.e. against the gel matrix, in a conventional manner not described. The advantage afforded by such a net is that the flow will be spread twice, i.e. once between the end plate and the perforated plate and once between the perforated plate and the net.

The adapter parts are conveniently manufactured separately, and preferably from stainless steel. The parts can be welded together for use in chromatography. The parts can be cleaned very easily and thus prevent undesirable contamination.

The inventive column is suitable for matrices having particle sizes of 5–250 μm, particularly for particle sizes of 5–60 μm, and flow rates of 50–1500 cm/h.

The use of the invention in application will now be illustrated with reference to a number of examples.

EXAMPLE 1

An inventive column tube having an inner diameter of 200 mm and a gel height of 30 mm was packed with 15 μm beads. The column was equalized with 0.5 M NaCl. A trace substance of 2.0 M NaCl with a sample volume corresponding to 1% of the gel volume was introduced to the column, whereafter the column was run with 0.5 M NaCl at a rate of flow of 60 cm/h. The conductivity was registered with a conductivity meter.

The peak was shown as a sharp peak and the plate number was calculated as N/L 26 300.

EXAMPLE 2

This example was run on two scales; a small scale with 2.2 ml gel and a column measuring internally 7.5 mm×50 mm, and on a large scale with 1570 ml gel and a column having internal dimensions of 200 mm×50 mm. In the small scale, the column was operated solely with nets, i.e. in the absence of perforated plates. In the large-scale test there was used a perforated plate in accordance with the invention. The particle size was 30 μm in both cases. The column was equalized with a 20 mM phosphate buffer, pH 6.8. Other conditions:

Sample: ribonuclease A, cytochrome C, lysozyme (3.75:1:1)

Amount of sample: 0.32 mg/ml gel

Flow rate: 300 cm/h

Buffer A: 20 mM phosphate buffer, pH 6.8

Buffer B: Buffer A+0.4 M NaCl

Gradient: 0–100% B, 10 column volumes.

Figure 4A:
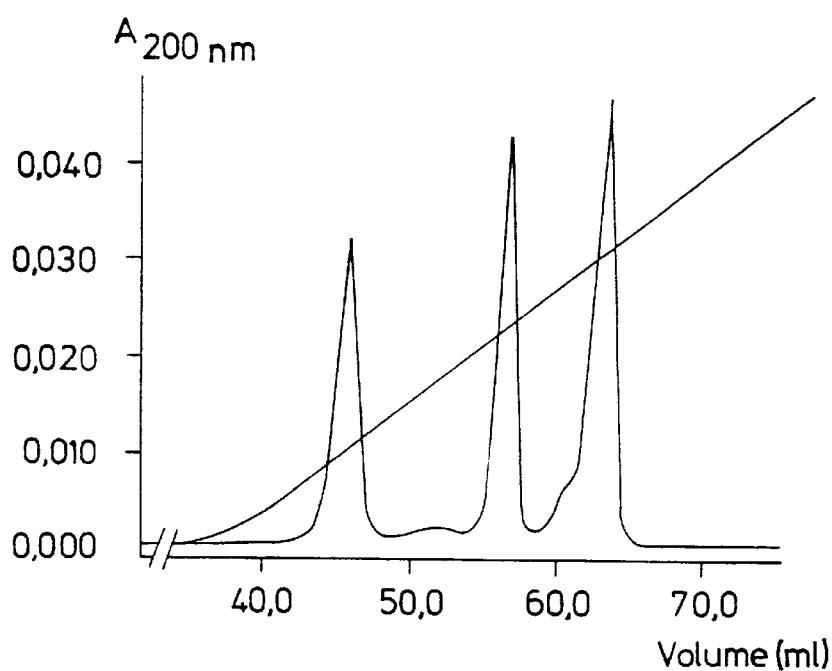
FIGS. 4a and 4b illustrate two chromatograms in small and large scale respectively, there being used an inventive column tube in the large-scale test.
Figure 4B:
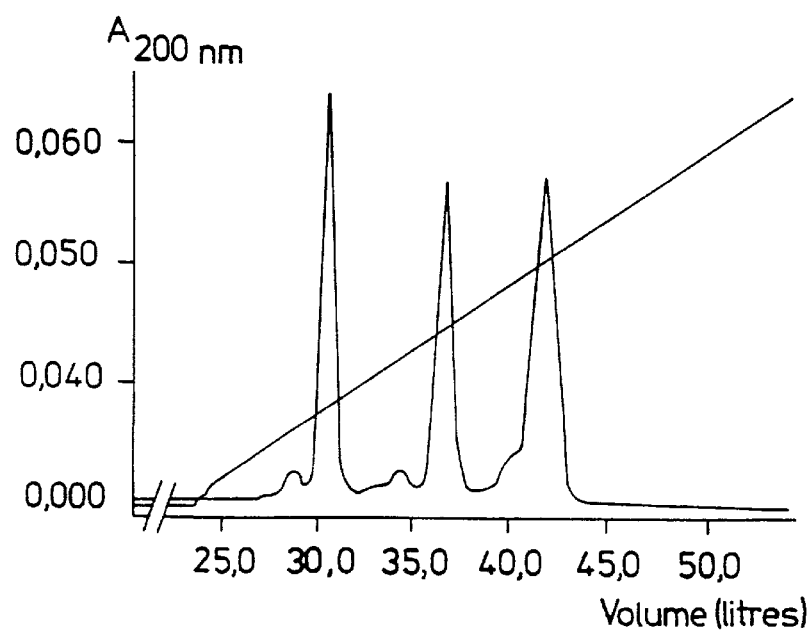

The results from Example 2 are shown in FIG. 4, wherein the upper chromatogram shows the result obtained with the small-scale test, and the lower chromatogram shows the result obtained with the large-scale test. It will be seen that three pronounced peaks occur in both instances. The resolution, i.e. the $R_s$-value, between the protein peaks for ribonuclease A (peak 1) and cytochrome C (peak 2) is 3.6 in the small scale and 3.6 in the large scale. The resolution between the protein peaks for cytochrome C (peak 2) and lysozyme (peak 3) is 2.2 in the small scale and 2.4 in the large-scale test.

Thus, despite the increase in diameter, the large-scale test gave an equally as good result as and even a better result than the small-scale test. Only unsatisfactory results have been achieved earlier. These results can now be greatly improved in accordance with the invention, with a column provided with adapters that include perforated plates.

What is claimed is:

1. A liquid-chromatography column constructed from a column tube that includes a chromatographic matrix, a flow inlet and a flow outlet and an adaptor placed at the inlet and outlet respectively, characterized in that the respective adaptors include an end-plate and a perforated plate configured to define a gap between the end-plate and the perforated plate, wherein said gap is created by projections on the end-late or the perforated plate and wherein the projections create a continuous vertical layer which allows continuous radial fluid flow across the end area of the matrix.

2. A column according to claim 1, characterized in that the gap has a depth of 0.2–1.0 mm.

3. A column according to claim 1, characterized in that the projections are circular.

4. A column according to claim 1, characterized by a net placed between matrix and perforated plate.

5. A column according to claim 1, characterized in that the column has a diameter of at least 50 mm.

6. A liquid-chromatography column constructed from a column tube that includes a chromatographic matrix, a flow inlet having a centrally located inlet opening and a flow outlet having a centrally located outlet opening, and an adaptor placed at the inlet and outlet respectively, characterized in that the respective adaptors include a planar end-plate and a planar perforated plate containing a plurality of openings, configured to define a single contiguous gap of greater than 0.2 mm between the end-plate and the perforated plate, wherein said gap is created by a plurality of discrete projections on the end-late or the perforated plate, wherein said projections on one of said plates contact the other of said plates to form said gap, and wherein the projections create a continuous vertical layer which allows continuous radial fluid flow across the end area of the matrix.

7. The method of claim 6, wherein said plurality of projections are formed on said perforated plate at points distinct from said plurality of openings.

8. The method of claim 6 or 7, wherein said projections have corresponding recesses on the opposite side of the plate on which the recesses are formed.

9. The method of claim 8, wherein said projections are round.

10. The method of claim 7, wherein a plurality of said projections are dispersed between a plurality of said openings.

11. The method of claim 7, wherein said plurality of projections are evenly distributed across said perforated plate.

12. The method of claim 7 or 11, wherein said plurality of openings are evenly dispersed across said perforated plate.

13. The method of claim 7, wherein a plurality of said projections are located half way between two adjacent holes.

* * * * *